United States Patent [19]

Hammond et al.

[11] Patent Number: 5,514,778
[45] Date of Patent: May 7, 1996

[54] ANTI-PICORNAVIRAL AGENTS

[75] Inventors: Marlys Hammond, Pasadena, Calif.; Stephen W. Kaldor, Indianapolis, Ind.

[73] Assignee: Eli Lilly and Company, Indianapolis, Ind.

[21] Appl. No.: 86,003

[22] Filed: Jul. 1, 1993

[51] Int. Cl.$^6$ ..................................... A61K 38/06
[52] U.S. Cl. .......................... 530/333; 530/331; 530/336; 530/345
[58] Field of Search ...................... 530/345, 333, 530/336, 331; 514/18, 19

[56] References Cited

FOREIGN PATENT DOCUMENTS

WO92/22570  12/1992  WIPO .............................. C07K 5/08

OTHER PUBLICATIONS

Hubert *Tetrahedron* 31 1437, 1975.
Araki *Tet Lett* 29, 351, 1988.
Chamberlin *Tet Lett* 23, 2619, 1982.
Skiles, et al., *Tetrahedron Letters*, "Spiro Indolinone Beta--Lactams, Inhibitors of Poliovirus and Rhinovirus 3C-Proteinases", 31:50, 7277–7280 (1990).
Cordingley, et al., *The Journal of Biological Chemistry*, "Substrate Requirements of Human Rhinovirus 3C Protease for Peptide Cleavage in Vitro", 265:16, 9062–9065 (1990).
Orr, et al., *J. Gen. Virol.*, "Hydrolysis of a Series of Synthetic Peptide Substrates by the Human Rhinovirus 14 3C Proteinase, Cloned and Expressed in *Escherichia coli*", 70, 2931–2942 (1989).
Nicklin, et al., *Biotechnology*, 4, (1986).
Takeda, et al., *Tetrahedron Letters*, "A Convenient Synthesis of Peptide Using Oxallates", 24, 4451–4455 (1983).
Witiak, et al., *J. Med. Chem*, "Para–Substituted N–Acetyl–L(S)–and–D(R)–alpha–amino–N–phenylsuccinimides and –glutarimides. Substituent Effects on Stereoselective Anticonsulvant Activity", 15, 1117–1123 (1972).
Stuart, et al., *Tetrahedron Letters*, "Isolation and Synthesis of Glutamine and Glutarimide Derivatives from Croton Humilis", 29, 4071–4075 (1973).
Wijnberg, et al., *Tetrahedron Letters*, "A Regioselective Reduction of Gem–Disubstituted Succinimides", 34, 179–187 (1978).

*Primary Examiner*—Christina Y. Chan
*Assistant Examiner*—David Lukton
*Attorney, Agent, or Firm*—Paul R. Cantrell

[57] ABSTRACT

The present invention provides a group of novel compounds that inhibit the proteolytic activity of 3C proteases which are found in picornaviruses, particularly rhinoviruses. In picornaviruses the RNA genome is translated into a single large viral polyprotein precursor. The precursor demonstrates auto-proteolytic activity, cleaving itself into mature viral gene products. Therefore, compounds of the current invention are particularly useful in treating picornaviral infections by interrupting the processing of the viral gene products into mature and infectious viral particles. The current invention also provides a novel process the preparation of compounds of the current invention. The process entails the selective reduction of an imide intermediate representing a marked improvement over processes known in the art for making peptidyl-aldehydes.

9 Claims, No Drawings

ANTI-PICORNAVIRAL AGENTS

BACKGROUND OF THE INVENTION

This invention relates to the discovery that a group of peptidyl-aldehydes is useful in the inhibition of picornaviral 3C proteases.

Picornaviridae are a family of very small non-enveloped viruses having a core of capsid-enclosed positive-stranded RNA. The picornaviruses represent a wide variety of microbes which infect a broad range of animals, including humans. Examples of picornaviruses include rhinoviruses, enteroviruses (e.g. poliovirus, coxsackievirus, echovirus), cardioviruses (e.g. encephalomyocarditis virus, meningovirus), aphthoviruses (e.g. foot-and-mouth disease virus), and hepatistis A virus, among others.

In picornaviruses the RNA genome is translated into a single large viral polyprotein precursor. The precursor demonstrates auto-proteolytic activity, cleaving itself into mature viral gene products. Proteolytic cleavage, therefore, plays an important role in the regulation of picornavirus replication and may thus represent an ideal target for antiviral therapy of all picornaviruses, including human rhinoviruses.

Human rhinoviruses (HRVs) are one of the major causes of upper respiratory tract infections collectively known as the common cold. Despite considerable effort in identifying therapeutics for this malady, no safe and effective therapy is currently available. Perhaps the most recalcitrant problem plaguing researchers in the area is the propensity for these viruses to mutate and thus develop resistance to potential medicaments. Vaccine therapy proves to be problematic for this very reason, and chemotherapy appears to be the more desirable approach.

In the case of the human rhinoviruses, there are two proteolytic enzymes involved, namely 2A and 3C, both of which are believed to be sulfhydryl proteases. Since these viral enzymes have no known cellular counterparts, it may be possible to selectively inhibit these enzymes in the presence of host enzymes. That is, chemotherapeutic agents having activity directed against the viral proteases would not affect endogenous cellular enzymes.

It appears that members of the picornavirus family may all code for a substantially homologous viral 3C protease, and in all picornaviruses studied, 3C protease activity is required for the virus to undergo maturation. Based on experience with other virally encoded proteolytic enzymes such as HIV-1 protease, it is unlikely that the viruses will develop resistance to inhibitors of these proteases. Moreover, the highly conserved nature of the 3C enzyme itself and the natural pressures on the virus to retain this highly efficient means for replication mark the suitability of the protease as a target for therapy.

Therefore, compounds that inhibit the proteolytic activity of the 3C protease are particularly useful in treating picornaviral infections by interrupting the processing of the viral gene products into mature and infectious viral particles.

SUMMARY OF THE INVENTION

The present invention provides a group of novel compounds that inhibit the proteolytic activity of 3C proteases which are found in picornaviruses, particularly rhinoviruses.

In particular, the present invention provides a compound of Formula I

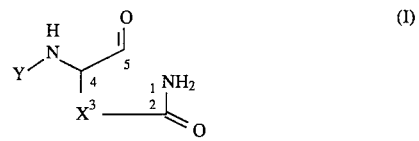

wherein
X is $(CR^1R^2)_n$;
Y is an amino acid or oligopeptide, an amino-protecting group, or $-C(O)R^3$;
n is 0, 1, 2, or 3;
$R^1$ and $R^2$ are independently selected from hydrogen, alkyl, alkylaryl, or aryl; and
$R^3$ is hydrogen, hydroxy, acyl, alkyl, arylalkyl, heteroarylalkyl, aryl, alkylaryl, heteroaryl, alkylheteroaryl, alkoxy, cycloalkoxy, arylalkoxy, heteroarylalkoxy, aryloxy, heteroaryloxy, cycloalkyl, heterocycle, unsaturated heterocycle, heterocyclooxy, unsaturated heterocyclooxy, alkylamino, cycloalkylamino, arylamino, heterocycloamino, unsaturated heterocycloamino, cycloalkylmethoxy, arylmethoxy, heterocyclomethoxy, unsaturated heterocyclomethoxy, alkylmethylamino, cycloalkylamino, arylmethylamino, heterocyclomethylamino, or unsaturated heterocyclomethylamino; or a pharmaceutically acceptable salt thereof.

3C Proteases function in the maturation and replication of picornaviruses by processing the polyprotein precursor encoded by the viral genome into the necessary mature proteins. Thus, the present invention also provides methods for treating a picornaviral infection by administering to an animal in need of treatment an antiviral amount of a compound or compounds which are 3C protease inhibitors.

The present invention also provides pharmaceutical formulations comprising as active ingredient a compound of Formula I in an amount that inhibits 3C protease activity, together with a pharmaceutically acceptable carrier, diluent, or excipient.

Another aspect of the invention is a process for preparing the compounds of Formula I which comprises acid-activating a compound of Formula II at a suitable temperature and reducing the imide intermediate of Formula III by treatment with a suitable reducing agent in an acidified hydroxylic solvent at a suitable temperature.

DETAILED DESCRIPTION OF THE INVENTION

The current invention concerns the discovery that a group of peptidyl-aldehydes of Formula I inhibit the activity of picornaviral 3C proteolytic enzymes.

All members of the picornaviral family, including human rhinoviruses, express a polyprotein precursor of which 3C protease is an element. The 3C protease is responsible for proteolytic cleavage of the polyprotein, and thus functions in regulating the maturation and replication of the virus by mediating viral component production and assembly. The compounds of the current invention, therefore, represent potential medical therapeutic agents for fighting picornaviral infections by preventing the processing of the precursor polypeptide. The inhibition of 3C proteolytic enzymes contemplated by the present invention also includes prophylactic methods as appropriate.

The peptidyl-aldehydes of Formula I appear not to interfere with the activity of proteases occurring naturally in host organisms thus demonstrating useful specificity for the viral enzyme.

For purposes of the present invention, as disclosed and claimed herein, the following terms and abbreviations are as defined below.
Boc—t-butyloxycarbonyl
Cbz—benzyloxycarbonyi
DCC—1,3-dicyclohexylcarbodiimide
DCU—dicyclohexylurea
DMSO—dimethylsulfoxide
DTT—dithiothreitol
EDTA—ethylenediaminetetraacetic acid
FITC—fluorescein isothiocyanate
HOBT—1-hydroxybenzotriazole hydrate
PAM—phenylacetimidomethyl
THF—tetrahydrofuran
TRIS—tris(hydroxymethyl)aminomethane The general chemical terms used in the description of this invention have their usual meanings.

References to "peptidyl-aldehydes" indicate compounds, such as those of Formula I, containing a peptide bond (a covalent link between a carboxyl group and an amino group) and a terminal -CH(O) group.

The term "imide" refers to a cyclic structure wherein a nitrogen, which itself constitutes part of the ring structure, is covalently linked on two sides by a carbonyl radical. For example, the imide function includes such structures as

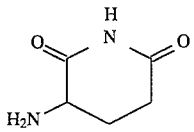

and radicals thereof.

The term "alkyl" by itself or as part of another substituent, unless otherwise stated, includes saturated straight or branched aliphatic hydrocarbon radicals such as methyl, ethyl, propyl, butyl, pentyl, hexyl, heptyl, and isomers and higher homologs of these radicals having the stated number of carbon atoms. The term "alkoxy" represents an alkyl group of the stated number of carbon atoms covalently attached through an oxygen bridge such as methoxy, ethoxy, propoxy, isopropoxy, butyloxy, and the like. In the context of the current invention, alkyl and alkoxy are preferrably limited to 10 carbon atoms or less.

The term "cycloalkyl" means a saturated ring group having the stated number of carbon atoms such as cyclopentyl, cyclohexyl, and cycloheptyl while the term "cycloalkoxy" means a saturated ring group covalently attached through an oxygen bridge having the stated number of carbon atoms which are linked through an oxygen molecule, such as cyclopentyloxy, cyclohexyloxy, and cycloheptyloxy. Such cyclic structures are preferrably limited to 8 carbon atoms or less.

Other chemical groups may also be attached through an oxygen bridge and likewise share the "oxy" terminology such as, for example, aryloxy, and heterocyclooxy. Similarly, chemical groups may be attached through an amino bridge leading to such groups as, for example, alkylamino, cycloalkylamino, and heterocycloamino where the attached group has the stated number of carbon atoms.

The term "acyl" refers to any group attached by means of the bivalent carbonyl radical. Such attached groups preferrably include hydrogen, alkyl, phenyl, and benzyl.

The term "aryl" means unsubstituted or substituted phenyl or unsubstituted or substituted naphthyl. The phenyl or naphthyl ring is unsubstituted or substituted with 1, 2, or 3 substituents independently selected from halo, $C_1$-$C_5$ alkyl, $C_1$-$C_5$ alkoxy, carboxy, ($C_1$-$C_4$ alkoxy)carbonyl, aminocarbonyl, $C_1$-$C_4$-alkylaminocarbonyl, amino, $C_1$-$C_4$ alkylamino, $C_1$-$C_4$ dialkylamino, benzyloxy or a group -$(CH_2)_q$-R where q is 1, 2, 3, or 4 and R is hydroxy, $C_1$-$C_4$ alkoxy, carboxy, $C_1$-$C_4$ alkoxycarbonyl, amino, aminocarbonyl, C1-C4 alkylamino or $C_1$-$C_4$ dialkylamino. The terms "halogen" and "halo" mean any of chloro, bromo, fluoro and iodo.

The term "heterocycle" means an unsubstituted or substituted stable 5- to 7-membered monocyclic ring and stable 7- to 10-membered bicyclic heterocyclic ring which is saturated and which consists of carbon atoms and from one to three heteroatoms selected from the group consisting of nitrogen, oxygen, and sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2, or 3 substituents independently selected from halo, $C_1$-$C_5$ alkyl, $C_1$-$C_5$ alkoxy, carboxy, ($C_1$-$C_4$ alkoxy)carbonyl, aminocarbonyl, $C_1$-$C_4$ alkylaminocarbonyl, amino, $C_1$-$C_4$ alkylamino, $C_1$-$C_4$ dialkylamino or a group -$(CH_2)_q$-R where q is 1, 2, 3, or 4 and R is hydroxy, $C_1$-$C_4$ alkoxy, carboxy, $C_1$-$C_4$ alkoxycarbonyl, amino, aminocarbonyl, $C_1$-$C_4$ alkylamino or $C_1$-$C_4$ dialkylamino.

The term "unsaturated heterocycle" has the same meaning as "heterocycle" except that the unsaturated heterocycle contains one or more double bonds.

Examples of such heterocycles and unsaturated heterocycles include piperidinyl, piperazinyl, 2-oxopiperazinyl, 2-oxopiperidinyl, 2-oxo-pyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl and tetrahydrisoquinolinyl.

The term "amino acid" is understood to include the 20 naturally-occurring amino acids; those amino acids often post-translationally modified in vivo, including, for example, hydroxyproline, γ-carboxyglutamate, phosphoserine, and phosphosyrosine, phosphothreonine; and other unusual amino acids including, for example, 2-aminoadipic acid, 3-aminoadipic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, isodesmosine, allo-isoleucine, N-methylglycine, N-methylisoleucine, N-methylvaline, norvaline, norleucine, and ornithine. Moreover, for purposes of this invention, "amino acids" refers to both D- and L-amino acids.

"Amino acid side chain" means the distinctive atom or group bonded to the Q-carbon atom of the amino acid. "Oligopeptide" refers to a series of amino acids linked by peptide bonds.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyi, 4 -phenylbenzyloxycarbonyl, 2-methylbenzyloxycarbonyl, 4-methoxybenzyloxycarbonyl, 4- fluorobenzyloxycarbonyl, 4 -chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3 -bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl-)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2 -methylcyclohexanyloxycarbonyl, 2-(4-toluylsulfonyl)ethoxycarbonyl, 2(methylsulfonyl)-ethoxycarbonyl, 2-(triphenylphosphino)ethoxycarbonyl, fluorenylmethoxycarbonyl (FMOC), 2-(trimethylsilyl)ethoxycarbonyl, allyloxycarbonyl, 1-(trimethylsilylmethyl)prop-1-enyloxycarbonyl, 5 -benzisoxalylmethoxycarbonyl, 4 -acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobronyloxycarbonyl, 1-piperidyloxycarbonyl and the like; the benzoylmethylsulfonyl group, the 2-(nitro)phenylsulfenyl group, the diphenylphosphine oxide group and like amino-protecting groups.

The species of amino-protecting group employed is not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are t-butyloxycarbonyl and benzyloxycarbonyl. Further examples of groups referred to by the above terms are described by J. W. Barton, *Protective Groups in Organic Chemistry* Chapter 2 (J. G. W. McOmie, ed., Plenum Press 1973); T. W. Greene, *Protective Groups in Organic Synthesis* Chapter 7 (John Wiley and Sons 1981)

The compounds of the present invention have at least one asymmetric center when referring specifically to the aldehyde tautomer of Formula I and at lease two asymmetric centers when referring specifically to the aminal tautomer of Formula I' as denoted by the asterisks in the formulas below.

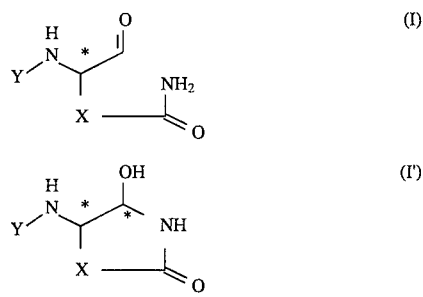

Further centers of asymmetry may also reside in Y.

As a consequence of these chiral centers, the compounds of the present invention occur as racemates, racemic mixtures and as individual diastereomers. All asymmetric forms, individual isomers and combinations thereof, are within the scope of the present invention.

As mentioned above, the invention includes pharmaceutically acceptable salts of the compounds defined by the above formula. Although generally neutral, a particular compound of this invention can possess a sufficiently acidic, a sufficiently basic, or both functional groups, and accordingly react with any of a number of nontoxic inorganic bases, and nontoxic inorganic and organic acids, to form a pharmaceutically acceptable salt.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromo-phenylsulfonic acid, carbonic acid, succinic acid, citric acid, benzoic acid, acetic acid, and the like.

Examples of such pharmaceutically acceptable sales thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxaiate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenyipropionate, phenylbutyrate, citrate, lactate, g-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

Preferred compounds of this invention are those of Formula I wherein R1 and R2 are both hydrogen, and in particular wherein X is $(CH_2)_2$, and, independently, wherein Y is an amino acid or oligopeptide or an amino-protecting group.

More preferred compounds of this invention are hose of Formula I wherein Y is an amino acid or oligopeptide and the amino acid is selected from, or the oligopeptide consists of, the 20 naturally-occurring amino acids.

Most preferred compounds of this invention are those of Formula I wherein X is $(CH_2)_2$ and Y is Boc-phenylalanyl-, 5-methylpentanoyl-phenylalanyl-, Boc-leucinyl-phenylalanyl-, Boc-valinyl-leucinyl-phenylalanyl-, N-acetyl-leucinyl-phenylalanyl-, N-acetyl-valinyl-leucinyl-phenylalanyl-, or valinyl-leucinyl-phenylalanyl-, and in particular wherein Y is Boc-valinyl-leucinyl-phenylalanyl- or Boc-leucinyl-phenylalanyl-;.

In Example 9, typical Formula I compounds were tested for their ability to inhibit the hydrolysis of a synthetic substrate by recombinant HRV 3C protease. The protease was cloned from the rhinovirus genome and recombinantly expressed in *E. coli*. Methods of acquiring HRV 3C protease in quantities sufficient for testing hydrolyric activity are described in the art (Nicklin, et al, (1986) Biotechnology 4:33–42; Orr, et al. (1989) J. Gen. Virol. 70:2931–42; Cordingly, et al. (1989) J. Virol. 63:5037–45).

The protease assay makes general use of the binding of a fluorescent component to solid particles followed by concentration and isolation of the particles from the reaction solution and quantitation of the signal using epifluorescence in order to determine the inhibitory capacity of potential antiviral compounds. In particular, the peptide arg-ala-glu-leu-gln-gly-pro-tyr-asp-glu-lys (SEQ ID NO:1) was synthesized by solid-phase peptide synthesis techniques using standard protocols. The peptide contains a sequence homologous to the naturally-occurring cleavage site off the HRV polyprotein and includes a gln-gly pair, which is the preferred cleavage site of all 3C proteases. Biotin was coupled to the amino-terminal arginine off the peptide, and FITC was then reacted with the carboxy terminus of the biotin-peptide, to generate the dually modified peptide substrate for the assay.

HRV 3C protease was preincubated with serial concentrations of peptide inhibitor followed by incubation with the synthetic substrate. The reaction mixture was then mixed with an excess of avidin-coated beads. As a result, the biotinylated peptide became immobilized onto the bead, which was then washed and collected by filtration on a 96-well Pandex Fluoricon Assay Plate (Idexx, Westbrook, Me.).

When the synthetic substrate is cleaved by the protease the biotinylated amino-terminal fragment is retained by the membrane while the FITC-containing carboxy-terminal fragment flows through the membrane and is discarded. However, in the presence of a 3C protease inhibitor, substrate cleavage is reduced and the resulting intact substrate molecules, including the fluorescent marker, bind to the avidin-coated beads and are retained by the membrane. Thus, an increase of fluorescence, measured in this instance by a Pandex Model 784 Screen Machine (Idexx, Westbrook, Me.) and compared to the incubation mixture without inhibitor, indicates an inhibitory effect.

The ability of the compounds of Formula I to inhibit 3C proteolytic activity and to fight picornaviral infection was also demonstrated by assay of in vitro translation of HRV RNA into mature proteins of the virus. In a cell-free translation system, when no inhibitor was present, RNA corresponding to the 2C'3ABCD portion of the HRV polypeptide precursor was translated into the various individual proteins of the virus. In contrast, the presence of Formula I inhibitors caused the RNA translation product to appear as a single unprocessed protein. The results of these translation assays are discussed in Example 10 and Table 1.

A third measure of antiviral activity was performed by determining the effects of selected 3C protease inhibitors of Formula I on HRV infection in cultures of Hela cells.

Commercially available Hela cells are susceptible to HRV infection. The virus enters the cells where it readily replicates and when infection levels become high enough, the Hela cells die. The effect of HRV inhibitors can be measured in Hela cultures by first exposing the cells to HRV and shortly thereafter (before viral infection becomes critical) adding potential inhibitors. Compounds which inhibit 3C protease activity serve to protect the cells from the cytopathic effect of the virus. Comparison of viability in cultures receiving serial dilutions of inhibitor to cultures not receiving any inhibitor allows quantization of the antiviral effect. Any toxic effect of the inhibitor can also be measured by comparing viability of treated cultures with those cultures which are not infected with the virus.

Viability determinations can be readily made by direct counts of viable cells or by assays representative of viability such as measurement of mitochondrial enzyme activity. The "XTT" assay of mitochondrial enzyme activity is described generally in Example 11 below and results are shown in Table 1.

Skilled artisans will recognize that the antiviral activity displayed in each of these assays by the compounds used in the present method is predictive of the utility of the compounds for use in vivo.

The picornaviral 3C protease inhibitors used in this invention can be prepared according to a novel process. Generally, the process comprises the reduction of an imide intermediate under conditions which selectively reduce the carbonyl at the 5 position to form the peptidylaldehyde final product.

The use of an imide intermediate represents a marked improvement over processes known in the art for making peptidyl-aldehydes. The imide protects the potentially reactive carboxamide-containing side chain in a relatively inert form, allowing a variety of chemical reactions to be performed with minimal competing side reactions.

Formation of the cyclic imide intermediate is accomplished by acid activating the carboxylic acid moiety of a carboxamide-containing amino acid, such as, for example, glutamine or asparagine, causing it to react with it's own carboxamide group thereby forming the cyclic imide.

Acid activation may be accomplished by a number of agents recognized in the art as being useful for such purposes. Preferred agents include carbodiimides, such as DCC (combined with reagents such as N-hydroxy-succinimide, nitrophenol, or HOBT). Other traditional activation agents such as acetic anhydride and acid chlorides may also be used. Useful activation agents cited by those skilled in the art include N,N'-carbonyldiimidazole, $POCl_3$, $PCl_5$, chloroformares, phenylenephosphorochloridite, chloroacetonitrile, pentafluorophenol, and the like (See M. Bodanszky, A. Bodanszky, *The Practice of Peptide Synthesis* (Klaus Hafner et al. eds., Springer-Verlag 1984)

The specific acid activator used affects the ability to produce stereochemically pure products. For example, acetic anhydride in the presence of amine bases leads to a racemic mixture of imide.

Although temperatures greater than 40° C. encourage progression of the activation reaction and are therefore preferred, a wide range of temperatures (0°–100° C.) is operable depending upon the type of agent being used. One of ordinary skill would be readily able to determine a suitable temperature.

The carboxamide-containing amino acid may be a variety of amino acids as defined above thus making possible the production of compounds having a variety of configurations at the carboxy terminus. The peptidyl portion of the inhibitors is also a source of variation which may be manipulated to afffect activity.

Discovery that the imide may be selectively reduced at the desired carbonyl represents a novel aspect of the current process. It would generally be expected that, under the reducing conditions stipulated, there would be little preference for reduction of either of the carbonyl groups over the other. However, it has been discovered that when $NaBH_4$ is used as the reducing agent in the presence of an acidified hydroxylic solvent, the carbonyl group at position 5 (as specifically depicted in Formula I) is reduced at a ratio of greater than 30 to 1 over the carbonyl at position 2 (as confirmed by Mosher amide analysis). Other less preferred reducing agents that lead to selective reduction of the carbonyl group at position 5 include metal borohydrides, such as zinc borohydride and sodiumcyanoborohydride; aluminum hydrides, such as diisopropylaluminum hydride and lithium aluminum hydride; and boranes, such as alkylborane and $BH_3 \bullet THF$.

Relative molar amounts of reducing agent to imide intermediate that are suitable for selective reduction of the imide are dependent upon the number of reducing groups present on the reducing agent. For example, suitable relative molar amounts of borohydrides range broadly from 1:4 to 20:1 (borohydride:imide). Preferred relative amounts range from 1:1 to 5:1.

Examples of hydroxylic solvents include water mixed with THF and an array of $C_1$-$C_6$ alcohols including, for example, methanol, ethanol, 1-propanol, 2-propanol, 1-butanol, 2-butanol, and 2-methyl-2-propanol, pentanol, hexanol, and cyclohexanol, all of which may have an aqueous content, or mixtures thereof. Preferrably, the solvent is 90% ethanol. Acidifying the solvent serves to catalyze the reaction. Suitable acids for such purposes include mineral acids. Preferred acids include HBr, $H_2SO_4$, and most preferrably HCl.

Suitable temperatures for the reduction reaction range from between about −80° C. to about 80° C. with about −10° C. to about 25° C. being preferred, about 0° C. to about 10° C. being more preferred, and about 0° C. being most preferred.

The resulting aldehydes are in equilibrium with the tautomeric aminal, which retains the cyclic nature of the imide at the carboxy terminus. This equilibrium is portrayed in the drawings of Scheme I below. The aldehyde tautomers are represented specifically by the configuration of Formula I while the aminal tautomers are represented by the configuration of Formula I'. For purposes of this disclosure, reference to the aldehyde products of Formula I also contemplates the tautomeric aminal configuration of Formula I'.

Scheme I:

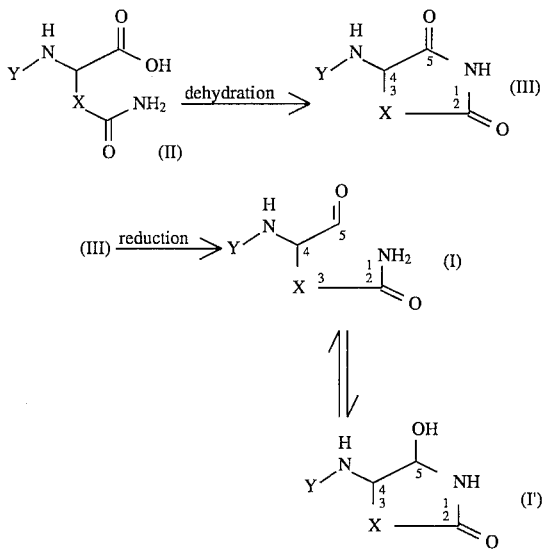

wherein

X is $(CR^1R^2)_n$;

Y is an amino acid or oligopeptide, an amino-protecting group, or $C(O)R^3$;

n is 0, 1, 2, or 3;

$R^1$ and $R^2$ are independently selected from hydrogen, alkyl, alkylaryl, or aryl; and $R^3$ is hydrogen, hydroxy, acyl, alkyl, arylalkyl, heteroarylalkyl, aryl, alkylaryl, heteroaryl, alkylheteroaryl, alkoxy, cycloalkoxy, arylalkoxy, heteroarylalkoxy, aryloxy, heteroaryloxy, cycloalkyl, heterocycle, unsaturated heterocycle, heterocyclooxy, unsaturated heterocyclooxy, alkylamino, cycloalkylamino, arylamino, heterocycloamino, unsaturated heterocycloamino, cycloalkylmethoxy, arylmethoxy, heterocyclomethoxy, unsaturated heterocyclomethoxy, alkylmethylamino, cycloalkylamino, arylmethylamino, heterocyclomethylamino, or unsaturated heterocyclomethylamino.

When Y is an amino acid or oligopeptide leading to preferred compounds of the current invention, Scheme I becomes Scheme Ia.

Scheme Ia:

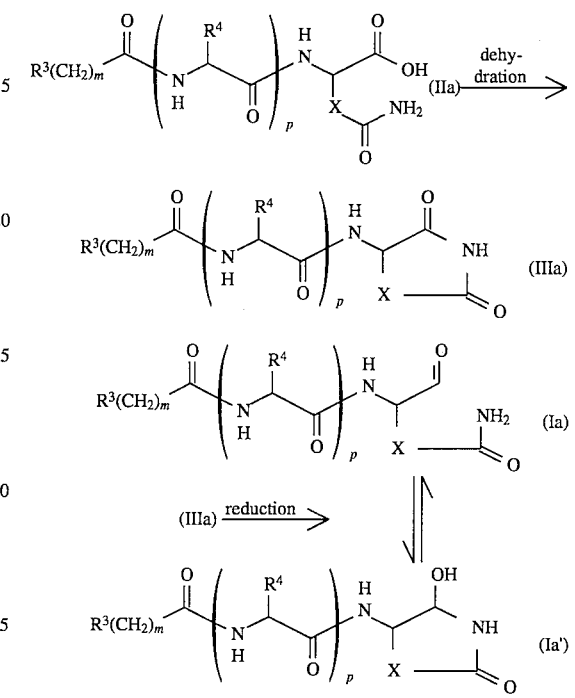

wherein $R^3$ and X have the same definitions as in Scheme I;

$R^4$ is an amino acid side chain;

m is 0, 1, 2, 3, or 4;

p is 0, 1, 2, 3, 4, or 5; and when p is greater than 1, the identity of each $R^4$ is independent of the other $R^4$ side chain(s).

Preferred amino acid side chains are those of the 20 naturally-occurring amino acids. More preferred amino acid side chains include those of phenylalanine, valine, and leucine.

Alternatively, according to Scheme II, the imide intermediate of Formula III wherein Y is an amino-protecting group, is deprotected to generate amino-imide intermediates of Formula IV that are stable and resistant to self reactivity.

The Formula IV intermediates are then acylated at the α-amine with a compound of Formula V

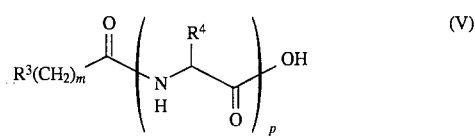

and again selectively reduced to generate desired aldehyde/ aminal compounds of Formulas Ia and Ia'.

Scheme II:

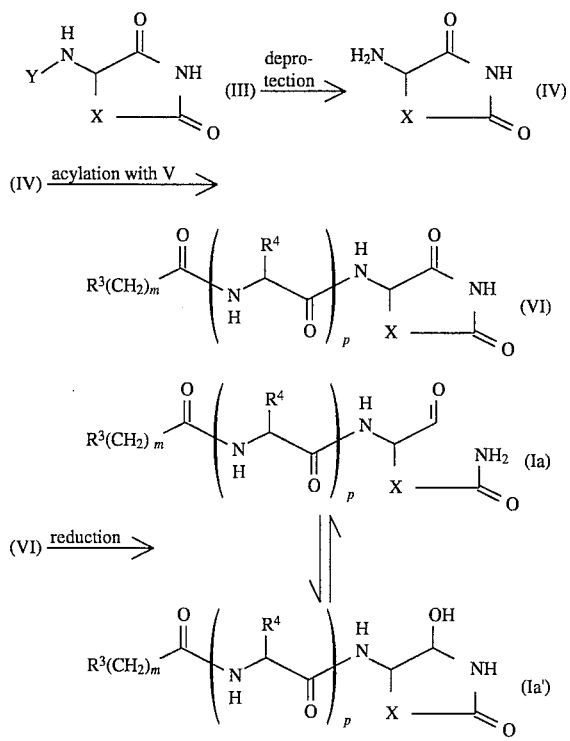

wherein $R^3$, $R^4$, X, Y, m, and p have the same definitions as above.

The process of Scheme III illustrates the possibility of further altering the order of the process steps. In all instances, the compounds produced may be maintained in protected form or may be deprotected as shown Scheme III.

Scheme III:

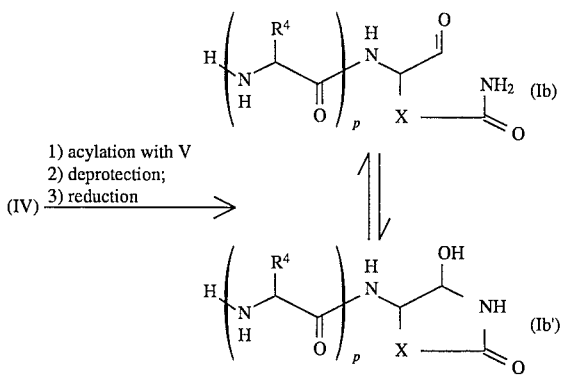

wherein $R^4$, X, and p have the same defintions as above.

The ordering of other manipulations such as deprotection of or coupling to other functional groups on the molecule can be varied according to the previously described schemes. For example, functional groups can be coupled to the Q-amine of the imide intermediate or to the reduced aldehyde. Thus, it is a matter of choice as to whether the imide intermediate is formed prior to or subsequent to attaching the desired peptidyl backbone.

Peptidyl portions which may be part of the current compounds can be synthesized by a variety of recognized techniques including classical (solution), solid-phase, and semisynthetic peptide synthetic methods. In the examples detailed below, solution methods were used to generate the specifically identified small peptides.

Solid phase chemical synthesis of polypeptides, which is well known in the art and may be found in general texts such as Dugas, H. and Penney, C., *Bioorganic Chemistry* (1981) Springer-Verlag, New York, pgs. 54–92, may also be employed to synthesize the straight chain portion of the peptidyl derivatives. For example, peptides may be synthesized by solid-phase methodology utilizing an Applied Biosystems 430A peptide synthesizer (commercially available from Applied Biosystems, Foster City Calif.) and synthesis cycles supplied by Applied Biosystems. Boc amino acids and other reagents are commercially available from Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Asparagine, glutamine, and arginine are coupled using preformed hydroxy benzotriazole esters. The following side chain protection may be used:

Arg, p-toluenesulfonyl
Asp, cyclohexyl
Glu, cyclohexyl
Ser, Benzyl
Thr, Benzyl
Tyr, 4-bromo-carbobenzoxy Boc deprotection may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of he side chain protecting group(s) and of the peptide from the resin is carried out at zero degrees centigrade or below, preferably −20° C. for thirty minutes followed by thirty minutes at 0° C. After removal of the HF, the peptide/resin is washed with ether, and the peptide extracted with glacial acetic acid and lyophilized. Purification is accomplished by size-exclusion chromatography on a Sephadex G-10 (Pharmacia) column in 10% acetic acid.

By substantially following the procedures described above one skilled in the art can prepare the compounds of Formula I.

The antiviral agents described above are active over a wide range of dose levels. This affords leeway to the attending medical practitioners to determine the specific dose of compound administered according to this invention in order to obtain the desired therapeutic and/or prophylactic effects. The circumstances of each case to consider include, for example, the precise vital infection to be treated or guarded against and its severity, the compound administered, and the route of administration.

Typically, a daily dose will contain a nontoxic dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

To practice the antiviral method of this invention, all that is required is that an antiviral amount of a Formula I compound be administered to an animal suffering from, or susceptible to, a viral infection by a variety of routes including oral, rectal, transdermal, subcutaneous, intravenous, intramuscular, and intranasal, or by other known methods. An "antiviral amount" is considered to be an amount that is effective in inhibiting the activity of the 3C protease. The compounds will ideally be formulated with pharmaceutically acceptable carriers, diluents, or excipients for convenient administration.

Therefore, another embodiment of the present invention is a pharmaceutical formulation comprising an effective amount of a compound of Formula I or a pharmaceutically acceptable salt thereof and a pharmaceutically acceptable carrier, diluent, or excipient therefor.

The formulations will normally contain from about 0.1% to about 99.9% by weight of active antiviral agent. By "pharmaceutically acceptable" it is meant the carrier, diluent or excipient must be compatible with the other ingredients of the formulation and not deleterious to the recipient thereof.

For severe viral infections, the antiviral compounds may be formulated for intravenous or intramuscular administration. Such formulations will generally contain from about 1 to about 50% active agent. The compounds will be dissolved in common diluents such as isotonic saline or dextrose solutions for intravenous infusion and can be dissolved in polyhydric aliphatic alcohols such as propylene glycol or polyethylene glycol for easy intravenous or intramuscular injection.

In a preferred method of treatment, the compounds are administered to mammals susceptible to infection with a picornavirus including horses, mice, pigs, sheep, and humans. Among humans, the compounds may be administered prophylactically, particularly to persons who are at risk of a picornaviral infection.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

For example, for parenteral administration, as by the intraperitoneal route, the compound may be dissolved or suspended in water containing 2% of a surface active agent, particularly an emulfor (a polyhydroxylated fatty acid). For intravenous administration, the compound can be dissolved in one of the commonly used intravenous fluids such as physiological saline, Ringer's solution, or 5% dextrose solution and the like. For intramuscular preparations, a sterile formulation containing a suitable salt form of the compound (for example, the hydrochloride salt or sodium salt) can be prepared with a suitable vehicle. Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

Further formulation examples are listed below. These examples are illustrative only and are not intended to limit the scope of the invention in any way. Ingredients and amounts to be used are listed along with a general description of how to make or use the formulations. "Active ingredient," of course, means a compound according to Formula I or a pharmaceutically acceptable salt thereof.

| Formulation 1 | |
|---|---|
| Hard gelatin capsules: | Quantity (mg/capsule) |
| Active ingredient | 250 |
| Starch, dried | 200 |
| Magnesium stearate | 10 |
| Total | 460 |

| Formulation 2 | |
|---|---|
| Tablets: | Quantity (mg/tablet) |
| Active ingredient | 250 |
| Cellulose, microcrystalline | 400 |
| Silicon dioxide, fumed | 10 |
| Stearic acid | 5 |
| Total | 665 |

The components are blended and compressed to form tablets each weighing 665 mg

| Formulation 3 | |
|---|---|
| Aerosol solutions: | Weight |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4 | |
|---|---|
| Tablets: | Quantity (mg/tablet) |
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

| Capsules: | Quantity (mg/capsule) |
| --- | --- |
| Active ingredient | 80 |
| Starch | 59 |
| Microcrystalline cellulose | 59 |
| Magnesium stearate | 2 |
| Total | 200 |

The active ingredient, cellulose, starch, and magnesium stearate are blended, passed through a No. 45 mesh U.S. sieve, and filled into hard gelatin capsules in 200 mg quantities.

Formulation 6

| Suppositories: | Quantity (mg/suppository) |
| --- | --- |
| Active ingredient | 225 |
| Saturated fatty acid glycerides | 2,000 |
| Total | 2,225 |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

| Suspensions (5 mL): | Quantity |
| --- | --- |
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

| Intravenous formulations: | |
| --- | --- |
| Active ingredient | 100 mg |
| Isotonic saline | 1,000 mL |

The solution of the above ingredients generally is administered intravenously to a subject at a rate of 1 mL per minute.

PREPARATIONS AND EXAMPLES

The following Preparations and Examples further illustrate the compounds of the present invention and methods for their synthesis. The examples are not intended to be limiting to the scope of the invention in any respect and should not be so construed.

The preparation of each titled compound as outlined in the examples below was confirmed by one or more of the following analytical methods: nuclear magnetic resonance spectroscopy (NMR), field desorption mass spectroscopy (FDMS), infrared spectroscopy (IR), optical rotation ([α]D), elemental analysis, high performance liquid chromatography (HPLC), and thin layer chromatography (TLC).

The absorption maxima listed for the IR spectra are only chose of interest and not all of the maxima observed. In addition, unless otherwise noted, NMR data appearing in the examples refers no the free base of the subject compound.

In conjunction with NMR spectra, the following abbreviations are used: "s" is singlet, "d" is doublet, "dd" is doublet of doublets, "t" is triplet, and "m" is multiplet. "J" indicates the coupling constant in Hertz. "DMSO-$d_6$" and "acetone-$d_6$" are dimethyl sulfoxide and acetone, respectively, where protons have been replaced with deuterium.

NMR spectra were obtained on a Varian Associates EM-390 90 MHz or T-60 60 MHz instrument, on a Jeol FX-90Q 90 MHz instrument, on a Brüker Corp. 270 MHz instrument or on a General Electric QE-300 300 MHz instrument. The chemical shifts are expressed in delta values (δ) (parts per million downfield from tetramethylsilane). The fast desorption mass spectra were obtained on a Varion-MAT 731 Spectrometer using carbon dendrite emitters. Infrared spectra were obtained on a Perkin-Elmer 281 instrument. Thin layer chromatography was carried out on E. Merck silica gel plates.

Preparation 1

N-tert-Butyloxycarbonyl-L-leucinyl-L-phenylalanine benzyl ester

A 500 mL round bottom flask under a nitrogen atmosphere was charged with 144 g (337 mmol) L-phenylalanine benzyl ester tosylate salt, 84 g (337 mmol) N-Boc-L-leucine, 46 g (337 mmol) HOBT, 37 mL (35 g, 337 mmol) 4-methyl morpholine (NMM), 150 mL anhydrous THF, and 50 mL N,N-dimethylformamide (DMF). The solution was cooled in an ice/acetone bath and 73 g (354 mmol) DCC was added in one portion. The mixture was stirred in the cold for 1 hour, and then warmed to room temperature and stirred overnight. The precipitated DCU was filtered off, and the filtrate was concentrated in vacuo. The residue was taken up in ethyl acetate and washed once with water, once with a 10% solution of citric acid, once with saturated sodium bicarbonate ($NaHCO_3$), and once with brine. The organic layer was then dried over sodium sulfate ($Na_2SO_4$), filtered, and concentrated in vacuo. The resultant solid was recrystallized from ethyl acetate/hexane to provide 67 g (42%) of the product dipeptide.

$[α]_D$ −25.13° (c 0.995, methanol) IR (KBr) 3344, 2958, 2935, 1735, 1681, 1666, 1521, 1167, 697 cm$^{-1}$ FDMS 468 (M$^+$), 468 (100) $^1$H NMR (300 MHz, CDCl$_3$) δ 0.87–0.89 (m, 6H), 1.42 (s, 9H), 1.56–1.60 (m, 3H), 3.09 (apparent t, J=5 Hz, 2H), 4.09–4.13 (m, 1H), 4.89 (dd, J=13, 6 Hz, 1H), 4.96–5.05 (m, 1H), 5.11 (dd, J=18 Hz, 12 Hz, 2H), 6.65 (d, J=7 Hz, 1H), 7.00–7.03 (m, 2H), 7.17–7.36 (m, 8H) Analytical calculated for $C_{27}H_{36}N_2O_4$: C 69.21, H 7.74, N 5,98; found C 69.02, H 7.98, N 6.12

Preparation 2

N-tert-Butyloxycarbonyl-L-leucinyl-L-phenylalanine

A solution of 5.00 g (10.7 mmol) N-tert-Butyloxycarbonyl-L-leucinyl-L-phenylalanine benzyl ester in 100 mL methanol was prepared. To this was added 6.7 g (107 mmol)

ammonium formate and 2.00 g 10% palladium on carbon (Pd/C). The solution was refluxed for 30 minutes and then cooled to room temperature. The catalyst was removed by filtration, and the filtrate was concentrated in vacuo. The residue was taken up in ethyl acetate, washed twice with 2N sodium bisulfate and once with brine. The organic layer was dried over $Na_2SO_4$, filtered, and concentrated in vacuo to provide 3.73 g (92%) of the desired acid which was used without any further purification.

$^1$H NMR (300 MHz, $CD_3OD$) δ 0.88 (d, J=9 Hz, 3H), 0.91 (d, J=9 Hz, 3H), 1.28–1.73 (m, 3H), 1.40 (s, 9H), 2.97 (dd, J=15, 7 Hz, 1H), 3.18 (dd, J=15, 5 Hz, 1H), 3.92–4.04 (m, 1H), 4.38–4.44 (m, 1H), 7.07–7.24 (m, 5H)

Preparation 3

N-tert-Butyloxycarbonyl-L-valinyl-L-leucinyl-L-phenylalanine benzyl ester

A 500 mL round bottom flask was charged with 46.52 g (99 mmol) N-tert-Butyloxycarbonyl-L-leucinyl-L-phenylalanine benzyl ester, 340 mL anhydrous m ethylene chloride ($CH_2Cl_2$), and 51 mL trifluoroacetic acid (TFA). The mixture was stirred at room temperature under a nitrogen atmosphere for 3 hours, and then concentrated in vacuo. The residue was azeotroped twice with toluene, and carried on. The same 500 mL round bottom flask containing the crude TFA salt was placed under a nitrogen atmosphere and charged with 21.5 g (99 mmol) Boc-L-valine, 13.4 g (99 mmol) HOBT, and 270 mL anhydrous THF The solution was cooled in an ice/acetone bath and 21.4 a (104 mmol) DCC was added in one portion. The mixture was stirred in the cold for 1 hour, and then warmed to room temperature and stirred overnight. The precipitated DCU was filtered off, and the filtrate was concentrated in vacuo. The residue was taken up in ethyl acetate and washed once with water, once with a 10% solution off citric acid, once with saturated $NaHCO_3$, and once with brine. The organic layer was then dried over $Na_2SO_4$, filtered, and concentrated in vacuo. The resultant solid was precipitated from ethanol with $H_2O$ to provide 41.96 g (75%) of the title compound.

$[α]_D$ –42.57° (c 1.01, methanol) IR ($CHCl_3$) 3246, 3027, 2965, 2936, 1736, 1675, 1497, 1171 $cm^{-1}$ FDMS 567 ($M^+$), 567 (100) $^1$H NMR (300 MHz, $CDCl_3$) δ 0.83–0.98 (m, 12H), 1.38–1.63 (m, 3H), 1.46 (s, 9H), 2.03–2.16 (m, 1H), 3.08 (apparent d, J=6 Hz, 2H), 3.83–3.91 (m, 1H), 4.37–4.46 (m, 1H), 4.82–4.89 (m, 1H), 5.02–5.17 (m, 3H), 6.40 (d, J=12 Hz, 1H), 6.54 (d, J=12 Hz, 1H), 6.99–7.02 (m, 2H), 7.14–7.38 (m, 8H) Analytical calculated for $C_{32}H_{45}N_3O_6$: C67.70, H 7.99, N 7.40; found C 67.64, H 7.80, N 7.30

Preparation 4

N-tert-Butyloxycarbonyl-L-valinyl-L-leucinyl-L-phenylalanine

A solution of 10.00 g (17.6 mmol) N-tert-Butyloxycarbonyl-L-valinyl-L-leucinyl-L-phenylalanine benzyl ester in 200 mL methanol was prepared. To this was added 11.1 g (176 mmol) ammonium formate and 5.00 g 10% Pd/C. The solution was refluxed for 30 minutes and then cooled to room temperature. The catalyst was removed by filtration, and the filtrate was concentrated in vacuo. The residue was taken up in ethyl acetate, washed twice with 2N sodium bisulfate and once with brine. The organic layer was dried over $Na_2SO_4$, filtered, and concentrated in vacuo to provide 10.07 g (quantitative yield) of the desired acid which was used without any further purification.

$[α]_D$ –27.00° (c 1.00, methanol) IR (KBr) 3300, 3249, 3138, 2979, 2929, 2875, 1735, 1675, 1650, 1516, 1249, 1154 $cm^{-1}$ FDMS 477 ($M^+$), 477(100) 1H NMR (300 MHz, CDCl3) δ 0.82–0.92 (m, 12H), 1.41–1.58 (m, 12H), 1.93–2.10 (m, 1H), 2.97–3.10 (m, 2H), 3.69–3.72 (m, 1H), 3.86–3.94 (m, 1H), 4.72–4.81 (m, 1H), 4.72–4.81 (m, 1H), 5.21 (d, J=12 Hz, 1H), 6.92–7.26 (m, 7H) Analytical calculated for $C_{25}H_{39}N_3O_6$: C 62.87, H 8.23, N 8.80; found C 62.60, H 8.11, N 8.56

Preparation 5

N-tert-Butyloxycarbonyl-L-valinyl-L-leucinyl-L-phenylalanylglycinenitrile

A 100 mL round bottom flask was charged with 1.00 g (2.09 mmol) N-tert-Butyloxycarbonyl-L-valinyl-L-leucinyl-L-phenylalanine, 185 mg (1.99 mmol) aminoacetonitrile hydrochloride, 260 mg (1.99 mmol) HOBT, 220 µL (202 mg, 1.99 mmol) NMM, 25 mL anhydrous THF, and 3 mL anhydrous DMF. The solution was cooled in an ice/acetone bath and 21.4 g (104 mmol) DCC was added in one portion. The mixture was stirred in the cold for 1 hour, and then warmed to room temperature and stirred overnight. The precipitated DCU was filtered off, and the filtrate was concentrated in vacuo. The residue was taken up in ethyl acetate and washed once with water, once with a 10% solution of citric acid, once with saturated $NaHCO_3$, and once with brine. The organic layer was then dried over $Na_2SO_4$, filtered, and concentrated in vacuo. The residue was purified by flash chromatography with 1:1 ethyl acetate/hexane to provide 781 mg (76%) of the title compound.

$[α]_D$ –51.28° (c 0.80, methanol) IR (KBr) 3290, 2964, 1643, 1534, 1367, 1246, 1172, 697 $cm^{-1}$ FDMS 515 ($M^+$), 515 (100) $^1$H NMR (300 MHz, acetone-$d_6$) δ 0.80 (apparent dd, J=10, 7 Hz, 6H), 0.88 (apparent t, J=7 Hz, 6H), 1.02–1.24 (m, 2H), 1.36 (s, 9H), 1.42–1.49 (m, 1H), 1.51–1.63 (m, 1H), 2.96 (dd, J=14, 9 Hz, 1H), 3.18 (dd, J=14, 5 Hz, 1H), 3.92 (dd, J=8, 7 Hz, 1H), 4.13 (d, J=6 Hz, 2H), 4.29 (dd, J=15, 6 Hz, 1H), 4.57 (dd, J=14, 8 Hz, 1H), 6.06 (d, J=7 Hz, 1H), 7.13–7.25 (m, 5H), 7.49 (d, J=8 Hz, 2H) , 7.85–7.91 (m, 1H) Analytical calculated for $C_{27}H_{41}N_5O_5$: C 62.89, H 8.01, N 13.58; found C 63.09, H 7.83, N 13.83.

Preparation 6

N-tert-Butyloxycarbonyl-L-valinyl-L-leucinyl-L-phenylalanylglycinal

A solution of 77 mg (0.15 mmol) N-tert-Butyloxycarbonyl-L-valinyl-L-leucinyl-L-phenylalanylglycinenitrile in 3 mL anhydrous THF was prepared in a flame-dried, 15 mL round bottom flask under a nitrogen atmosphere. The solution was cooled to 0° C., and 780 µL 1.0M diisobutylaluminum hydride (DIBAl) in toluene. The solution was stirred at 0° C. for two minute, and then warmed to room temperature and stirred for 1 hour. The reaction was quenched with 5 drops of methanol followed by 5 drops $H_2O$. The mixture was filtered, and the filtrate concentrated in vacuo. The residue was taken up in ethyl acetate and dried over $Na_2SO_4$. Rotary chromatography with 9:1 $CH_2Cl_2$/methanol afforded 16 mg (21%) of the title compound.

FDMS 519 (M⁺), 519 (100) H NMR (300 MHz, CDCl$_3$) δ 0.84–0.88 (m, 12H), 1.03–1.18 (m, 1H), 1.40 (s, 9H), 1.48–1.74 (m, 3H), 1.88–2.06 (m, 2H), 3.00 (dd, J=14, 8 Hz, 1H), 3.10 (dd, J=14, 8 Hz, 1H), 3.39–3.48 (m, 1H), 3.95 (apparent d, J=5 Hz, 1H), 4.04–4.08 (m, 1H), 4.56 (dd, J=12, 5 Hz, 1H), 4.94 (dd, J=12, 4 Hz, 1H), 5.32 (d, J=8 Hz, 1H), 7.15–7.54 (m, 6H), 9.39 (s, 1H)

Preparation 7

N-Benzyloxycarbonyl-L-glutarimide

A 500 mL round bottom flask was charged with 25 g (217 mmol) N-hydroxysuccinimide, 61 g (217 mmol) N-Cbz-glutamine, 150 mL anhydrous THF, and 45 mL anhydrous DMF. The solution was cooled in an ice/acetone bath, and 45 g (217 mmol) DCC was added in one portion. The mixture was stirred and allowed to gradually warm to room temperature overnight. Next, the DCU was removed by filtration and the filtrate concentrated in vacuo. The residue was taken up in approximately 300 mL chloroform (CHCl$_3$) and refluxed for three hours. The chloroform was removed by rotary evaporation, and the residue was taken up in ethyl acetate, washed three times with water and once with brine. The organic layer was dried over Na$_2$SO$_4$, filtered, and concentrated in vacuo. The solid residue was triturated with ethyl acetate to provide 41.17 g (71%) of the title compound.

[α]$_D$ −56.86° (c 1.02, methanol) IR (KBr) 3353, 3095, 1708, 1691, 1535, 1365, 1255, 1192, 741 cm⁻¹ FDMS 262 (M⁺), 262 (100) ¹H NMR (300 MHz, CDCl$_3$) δ 1.92 (ddd, J=26, 13, 5 Hz, 1H), 2.52–2.83 (m, 3H), 4.34–4.40 (m, 1H), 5.13 (apparent s, 2H), 5.63 (d, J=5 Hz, 1H), 7.35 (apparent s, 5H), 8.23 (s, 1H) Analytical calculated for C$_{13}$H$_{14}$N$_2$O$_4$: C 59.54, H 5.38, N 10.68; found C 59.26, H 5.09, N 10.67

Example 1

[S-(R*,S*)]-5-N-Benzyloxycarbonylamino-6-hydroxypiperidine-2-one and
[S-(R*,R*)]-5-N-Benzyloxycarbonylamino-6-hydroxypiperidine-2-one A 50 mL flask was charged with 500 mg (1.91 mmol) N-benzyloxycarbonyl-L-glutarimide and 20 mL 90% ethanol. The solution was cooled to 0° C. and 289 mg (7.64 mmol) sodium borohydride (NaBH$_4$) was added in one portion followed by three drops of 2N HCl. The solution was stirred at 0° C., and two drops of 2N HCl were added every fifteen minutes for one hour. The reaction was quenched at 0° by adding 2N HCl dropwise until a pH of 3 was reached. The reaction was then stirred at 0° C. for an additional 1.5 hours. The reaction mixture was then poured into 20 mL water and extracted three times with CHCl$_3$. The combined organic layers were dried over Na$_2$SO$_4$, filtered, and concentrated in vacuo. The residue was purified by rotary chromatography with 3:2 CH$_2$Cl$_2$/methanol to provide 445 mg (88%) of the title compound.

IR (KBr) 3435, 1064, 1244, 577 cm⁻¹ FDMS 265 (M⁺), 265 (100) ¹H NMR (300 MHz, CDCl$_3$—major diastereomer given) δ 1.63–1.77 (m, 1H), 1.89–2.20 (m, 1H), 2.24–2.40 (m, 2H), 3.75–3.97 (m, 1H), 4.73–4.84 (m, 1H), 4.99–5.16 (m, 2H), 5.62–5.76 (m, 1H), 7.22–7.38 (m, 5H), 7.78 (s, 1H)

Preparation 8

L-Glutarimide

A solution of 10.00 g (38 mmol) N-benzyloxycarbonyl-L-glutarimide in 200 mL ethanol was prepared in a 500 mL round bottom flask. The flask was covered with a rubber septum, and nitrogen was bubbled through the solution for 20 minutes to degas the solution. The flask was equipped with a reflux condenser, and under a nitrogen atmosphere, 4.00 g 10% Pd/C was added, followed by 30 mL (25 g, 320 mmol) 1,4-cyclohexadiene. The solution was heated with a heat gun to initiate the reaction. After an additional 30 minutes, the catalyst was removed by filtration through celite, and the filtrate was concentrated in vacuo. The slightly unstable product was used directly in couplings without further purification or characterization.

Preparation 9

N-tert-Butyloxycarbonyl-L-phenylalanyl-L-glutarimide

A solution of 1.00 g (7.80 mmol) L-glutarimide, 2.17 g (8.19 mmol) Boc-L-phenylalanine, 1.11 g (8.19 mmol) HOBT, and 50 mL anhydrous THF was prepared in a 250 mL round bottom flask. The solution was cooled in an ice/acetone bath, and 1.64 g (7.96 mmol) DCC was added in one portion. The reaction was stirred in the cold for one hour, and then allowed to warm to room temperature and stir for two additional hours. The DCU was removed by filtration, and the filtrate concentrated in vacuo. The residue was dissolved in hot ethanol and cooled. Precipitation was induced by the addition of hexanes. The product (1.59 g, 54%) was isolated by filtration.

[α]$_D$ −33.33° (c 1.05, methanol) IR (KBr) 3267, 3074, 1717, 1681, 1656, 1562, 1539, 1250, 1162, 1019 cm⁻¹ FDMS 375 (M⁺), 375 (100) ¹H NMR (300 MHz, CD$_3$OD) δ 1.34 (s, 9H), 1.95–2.05 (m, 1H), 2.08–2.20 (m, 1H), 2.59–2.78 (m, 2H), 2.81 (dd, J=12, 9 Hz, 1H), 3.15 (dd, J=12, 4 Hz, 1H), 4.30–4.38 (m, 1H), 4.59 (dd, J=12, 6 Hz, 1H), 7.13–7.28 (m, 5H) Analytical calculated for C$_{19}$H$_{25}$N$_3$O$_5$: C 60.79, H 6.71, N 11.19; found 60.90, H 6.76, N 11.04

Example 2

[S-(R*,S*)]-5-(N-tert-butoxycarbonyl-L-phenylalanyl)amino-6-hydroxypiperidine-2-one and
[S-(R*,R*)]-5-(N-tert-butoxycarbonyl-L-phenylalanyl)amino-6-hydroxypiperidine-2-one A 15 mL flask was charged with 100 mg (0.27 mmol) N-tert-Butyloxycarbonyl-L-phenylalanyl-L glutarimide and 2 mL 90% ethanol. The solution was cooled to 0° C. and 31 mg (0.83 mmol) NaBH$_4$ was added in one portion followed by one drop of concentrated HCl. The solution was stirred at 0° C., and one drop of concentrated HCl was added every fifteen minutes for one hour. The reaction was then stirred at 0° C. for an additional hour. The reaction mixture was then poured into 10 mL water and extracted three times with CHCl$_3$. The combined organic layers were dried over Na$_2$SO$_4$, filtered, and concentrated in vacuo. The residue was purified by rotary chromatography with a gradient of 100% CH$_2$Cl$_2$ to 4:1 CH$_2$Cl$_2$/methanol to provide 52 mg (51%) of the title compound.

[α]$_D$ +16.00° (c 0.25, methanol) IR (KBr) 3308, 3066, 3031, 2978, 2934, 1657, 1531, 1497, 1367, 1251, 1169, 1042 cm⁻¹ FDMS 377(M⁺), 377(100) ¹H NMR (300 MHz, CDCl$_3$) (diagnostic peaks only) δ 1.36 (s, 9H, t-butyl), 2.99–3.01 (m, 2H, benzylics), 7.16–7.30 (m, 5H, aromatics) Analytical calculated for C$_{19}$H$_{27}$N$_3$O$_5$: C 60.46, H 7.21, N 11.13; found C 60.65, H 7.32, N 10.99

Preparation 10

N-5-methylpentanoyl-L-phenylalanyl-L-glutarimide

A solution of 800 mg (2.13 mmol) N-tert-Butyloxycarbonyl-L-phenylalanyl-L glutarimide in 16 mL $CH_2Cl_2$ was prepared in a 50 mL round bottom flask. A total of 2.4 mL TFA was added. After one hour the reaction was concentrated in vacuo and azeotroped twice with toluene. A portion of this TFA salt (200 mg, 0.51 mmol) was placed in a 10 mL flame-dried round bottom flask under a nitrogen atmosphere along with 143 μL (104 mg, 1.03 mmol) triethylamine In a separate flask, 2 mL benzene, 47 μL (76 mg, 0.65 mmol) thionyl chloride, and 1 drop DMF were combined. This was followed by dropwise addition of 65 μL (60 mg, 0.51 mmol) 4-methylpentanoic acid. The flask was equipped with a reflux condenser, and the solution was refluxed for 1.5 hours. The reaction mixture was cooled to room temperature and concentrated in vacuo. The residue was dissolved in 1 mL anhydrous THF and added via syringe to the previously prepared solution containing the TFA salt. The reaction was stirred at room temperature for one hour, and then concentrated in vacuo. The residue was taken up in ethyl acetate and washed once with water, once with 10% citric acid, once with saturated $NaHCO_3$, and once with brine. The organic layer was dried over Na2SO4, filtered and concentrated in vacuo. Purification was accomplished using rotary chromatography with a gradient of 100% $CH_2Cl_2$ to 9:1 $CH_2Cl_2$/methanol, affording 71 mg (37%) of the title compound.

$[\alpha]_D$ −31.03° (C 0.29, methanol) IR (KBr) 3292, 3087, 2957, 2870, 1712, 1645, 1541, 1196, $cm^{-1}$ FDMS 373 ($M^+$), 373 (100) 1H NMR (300 MHz, CDCl3) δ 0.80–0.83 (m, 6H), 1.36–1.41 (m, 3H) , 1.89–2.04 (m, 1H) , 2.11–2.23 (m, 3H) , 2.61–2.67 (m, 2H), 2.98 (dd, J=14, 8 Hz, 1H), 3.12 (dd, J=14, 6 Hz, 1H), 4.44 (apparent pentuplet, J=6 Hz, 1H), 4.87 (dd, J=14, 6 Hz, 1H), 6.72 (d, J=8 Hz, 1H), 7.17–7.25 (m, 5H), 7.56 (d, J=7 Hz, 1H), 8.82–9.40 (br s, 1H) Analytical calculated for $C_{20}H_{27}N_3O_4$: C 64.32, H 7.29, N 11.25; found C 64.29, H 7.19, N 11.11

Example 3

[S-(R*,S*)]-5-(N-5'-methylpentanoyl-L-phenylalanyl)amino-6-hydroxypiperidine-2-one and [S-(R*,R*)]-5-(N-5'-methylpentanoyl-L-phenylalanyl)amino-6-hydroxypiperidine-2-one A 10 mL flask was charged with 56 mg (0.15 mmol) N-5-methylpentanoyl-L-phenylalanyl-L-glutarimide and 2 mL 90% ethanol. The solution was cooled to 0° C. and 20 mg (0.52 mmol) $NaBH_4$ was added in one portion followed by one drop of concentrated HCl. The solution was stirred at 0° C., and one additional drop of concentrated HCl was after fifteen minutes. After a total time of 30 minutes, the reaction was then stirred at 0° C. for an additional hour. The reaction mixture was then poured into 10 mL water and extracted three times with $CHCl_3$. The combined organic layers were dried over $Na_2SO_4$, filtered, and concentrated in vacuo. The residue was purified by rotary chromatography with a gradient of 9:1 $CH_2Cl_2$/methanol to 4:1 $CH_2Cl_2$/methanol to provide 43 mg (76%) of the title compound.

$[\alpha]_D$ +40.00° (c 0.15, methanol) IR (KBr) 3286, 3067, 2957, E871, 1644, 1550, 1497, 1055, 699 $cm^{-1}$ FDMS 375 ($M^+$), 375 (100) $^1$H NMR (300 MHz, $CD_3OD$—major diastereomer given) δ 0.81–0.83 (m, 6H), 1.26–1.42 (m, 3H), 1.70–1.76 (m, 1H), 2.09–2.21 (m, 3H), 2.28–2.41 (m, 2H), 2.88 (dd, J=14, 8 Hz, 1H), 3.03 (dd, J=14, 6 Hz, 1H), 3.91–3.93 (m, 1H), 4.53–4.55 (m, 1H), 4.61 (dd, J=15, 8 Hz, 1H), 7.15–7.27 (m, 5H), 8.07–8.11 (m, 2H)

Preparation 11

N-tert-Butoxycarbonyl-L-leucinyl-L-phenylalaninyl-L-glutarimide

A solution of 456 mg (1.20 mmol) N-tert-Butyloxycarbonyl-L-leucinyl-L-phenylalanine, 147 mg (1.14 mmol) L-glutarimide, 163 mg (1.20 mmol) HOBT, 10 mL anhydrous THF, and 1 mL anhydrous DMF was prepared in a 25 mL round bottom flask. The solution was cooled in an ice/acetone bath, and 241 mg (1.17 mmol) DCC was added in one portion. The reaction was stirred in the cold for one hour, and then allowed to warm to room temperature and stir for five additional hours. The DCU was removed by filtration, and the filtrate concentrated in vacuo. The residue was taken up in ethyl acetate and washed once with water, once with 10% citric acid, once with saturated $NaHCO_3$, and once with brine. The organic layer was dried over $Na_2SO_4$, filtered, and concentrated it vacuo. Rotary chromatography with 9:1 $CH_2Cl_2$/methanol afforded 442 mg (79%) of the title compound.

$[\alpha]_D$ −47.76° (c 0.67, methanol) IR ($CHCl_3$) 3026, 2967, 2935, 1714, 1498, 1369, 1246 $cm^{-1}$ FDMS 488 ($M^+$), 488 (100) 1H NMR (300 MHz, $CDCl_3$) δ 0.87–0.91 (m, 6H), 1.05–1.86 (m, 3H), 1.44 (s, 9), 2.22–2.32 (m, 1H), 2.69–2.71 (m, 2H), 3.07–3.21 (m, 2H), 4.25–4.27 (m, 1H), 4.51–4.55 (m, 1H), 4.82–4.86 (m, 1H), 5.08 (d, J=7 Hz, 1H), 7.07–7.31 (m, 7H), 7.51 (d, J=6 Hz, 1H), 9.18 (s, 1H)

Example 4

[S-(R*,S*)]-5-(N-tert-butoxycarbonyl-L-leucinyl-L-phenylalanyl)amino-6-hydroxypiperidine-2-one and [S-(R*,R*)]-5-(N-tert-butoxycarbonyl-L-leucinyl-L-phenylalanyl)amino-6-hydroxypiperidine-2-one A 10 mL flask was charged with 100 mg (0.20 mmol) N-tert-Butoxycarbonyl-L-leucinyl-L-phenylalaninyl-L-glutarimide and 2 mL 90% ethanol. The solution was cooled to 0° C. and 31 mg (0.81 mmol) $NaBH_4$ was added in one portion followed by 10 μL of concentrated HCl. The solution was stirred at 0° C., and an additional 10 μL of concentrated HCl was added after ten minutes. After a total time of 20 minutes, the reaction was then stirred at 0° C. for an additional two hours. The reaction mixture was then poured into 10 mL water and extracted three times with $CHCl_3$. The combined organic layers were dried over $Na_2SO_4$, filtered, and concentrated in vacuo. The residue was purified by rotary chromatography with a gradient of 100% $CH_2Cl_2$ to 3:1 $CH_2Cl_2$/methanol to provide 55 mg (56%) of the title compound.

$[\alpha]_D$ −30.00° (c 0.30, methanol) IR (KBr) 3326, 2961, 2873, 1690, 1647, 1525, 1170, 1047 $cm^{-1}$ FDMS 493 ($M^+$), 493 (100) $^1$H NMR (300 MHz, acetone-$d_6$) δ 0.81–0.86 (m, 6H), 1.35 (s, 9H), 1.46 (apparent t, J=7 Hz, 1H) , 1.58–1.63 (m, 2H), 1.83–2.00 (m, 1H), 2.15 (apparent t, J=7 Hz, 2H), 2.94 (dd, J=13, 8 Hz, 1H), 3.07 (dd, J=13, 6 HZ, 1H), 3.25 (s, 1H), 3.29–3.46 (m, 2H), 3.79–3.83 (m, 1H), 4.03 (dd, J=11, 4 Hz, 1H), 4.55–4.60 (m, 1H), 6.15–6.19 (m, 1H), 6.21–6.24 (m, 1H), 6.83–6.86 (m, 1H), 7.16–7.20 (m, 5H), 7.39 (d, J=7 Hz, 1H) Analytical calculated for $C_{25}H_{38}N_4O_6$: C. 21, H 7.87, N 1.42; found C 61.34, H 8.13, N 11.38

Preparation 12

N-tert-Butoxycarbonyl-L-valinyl-L-leucinyl-L-phenylalanyl-L-glutarimide

A solution of 4.34 g (8.19 mmol) N-tert-Butyloxycarbonyl-L-valinyl-L-leucinyl-L-phenylalanine 1.00 g (7.80 mmol) L-glutarimide, 1.11 g (8.19 mmol) HOBT, 50 mL anhydrous THF, and 5 mL anhydrous DMF was prepared in a 100 mL round bottom flask. The solution was cooled in an ice/acetone bath, and 1.46 g (7.96 mmol) DCC was added in one portion. The reaction was stirred in the cold for one hour, and then allowed to warm to room temperature and stir for three additional hours. The DCU was removed by filtration, and the filtrate concentrated in vacuo. The residue was taken up in ethyl acetate and washed once with water, once with 10% citric acid, once with saturated NaHCO$_3$, and once with brine. The organic layer was dried over Na$_2$SO$_4$, filtered, and concentrated in vacuo. Rotary chromatography with a gradient of 100% CH$_2$Cl$_2$ to 9:1 CH$_2$Cl$_2$/methanol afforded 3.12 g/68% of the title compound.

$[\alpha]_D$ −63.01° (c 0.70, methanol) IR (KBr) 3291, 3088, 2963, 2934, 2873, 1713, 1642, 1524, 1367, 1196 cm$^{-1}$ FDMS 587(M$^+$), 587(100) $^1$H NMR (300 MHz, DMSO-d$_6$) δ 0.68–0.80 (m, 12H), 1.20–1.40 (m, 1H), 1.32 (s, 9H), 1.43–1.58 (m, 1H), 1.79–1.85 (m, 3H), 2.42–2.48 (m, 2H), 2.67 (dd J=14, 8 Hz, 1H), 2.81 (dd, J=14, 9 Hz, 1H), 3.02 (dd, J=14, 4 Hz, 1H), 3.69 (apparent t, J=9 Hz, 1H), 4.25 (dd, J=14, 6 Hz, 1H), 4.46–4.53 (m, 2H), 6.68 (d, J=9 Hz, 1H), 7.09–7.19 (m, 5H), 7.72 (d, J=8 Hz, 1H), 7.87 (d, J=8 Hz, 1H), 8.25 (d, J=8 Hz, 1H), 10.77 (s, 1H) Analytical calculated for C$_{30}$H$_{45}$N$_5$O$_7$: C 61.31, H 7.72, N 11.92; found C 61.51, H 7.72, N 11.94

Example 5

[S-(R*,S*)]-5-(N-tert-butyloxycarbonyl-L-valinyl-L-leucinyl-L-phenylalanyl)amino-6-hydroxypiperidine-2-one and [S-(R*,R*)]-5-(N-tert-butyloxycarbonyl-L-valinyl-L-leucinyl-L-phenylalanyl)amino-6-hydroxypiperidine-2-one A 10 mL flask was charged with 100 mg (0.17 mmol) N-tert-Butoxycarbonyl-L-valinyl-L-leucinyl-L-phenylalaninyl-L-glutarimide and 2 mL 90% ethanol. The solution was cooled to 0° C. and 26 mg (0.68 mmol) NaBH$_4$ was added in one portion followed by 1 drop of concentrated HCl. The solution was stirred at 0° C., and an additional 1 drop of concentrated HCl was added every fifteen minutes for thirty minutes. After a total time of 45 minutes, the reaction was then stirred at 0° C. for an additional two hours. The reaction mixture was then poured into 10 mL water and extracted three mimes with CHCl$_3$. The combined organic layers were dried over Na$_2$SO$_4$, filtered, and concentrated in vacuo. The residue was purified by rotary chromatography with 98:2 CH$_2$Cl$_2$/methanol to provide 72 mg (72%) of the title compound.

$[\alpha]_D$ −45.65° (C 0.92, methanol) IR (KBr) 3289, 2963, 1641, 1523, 1367, 1173, 699 cm$^{-1}$ FDMS 589 (M$^+$), 589 (100) $^1$H NMR (300 MHz, DMSO-d$_6$—major diastereomer given) δ 0.73–0.81 (m, 12H), 1.32 (s, 9H), 1.49–1.53 (m, 3H), 1.82–1.85 (m, 1H), 2.02–2.06 (m, 2H), 2.21–2.28 (m, 1H), 2.71–2.79 (m, 1H), 2.84–2.86 (m, 1H), 3.66–3.71 (m, 2H), 4.22–4.26 (m, 1H), 4.44–4.48 (m, 1H), 4.50–4.54 (m, 1H), 5.85 (d, J=5 Hz, 1H), 6.69 (d, J=8 Hz, 1H), 7.12–7.18 (m, 6H), 7.71–7.85 (m, 3H), 7.97 (d, J=13 Hz, 1H)

Preparation 13

N-Acetyl-L-leucinyl-L-phenylalanyl-L-glutarimide

A solution of 500 mg (1.02 mmol) N-tert-Butoxycarbonyl-L-leucinyl-L-phenylalaninyl-L-glutarimide in 15 mL CH2C12 and 2.3 mL TFA was prepared. The reaction was stirred for one hour and then concentrated in vacuo. The residue was then azeotroped twice with toluene and dissolved in 15 mL CH2C12 in a 25 mL round bottom flask under nitrogen. To this solution was added 284 μL (206 mg, 2.04 mmol) triethylamine and 73 μL (80 mg, 1.02 mmol) acetyl chloride. The reaction was stirred at room temperature for 30 minutes and then washed twice with 10% citric acid and once with brine. The organic layer was dried over Na$_2$SO$_4$, filtered and concentrated in vacuo. Rotary chromatography provided 228 mg (52%) of the title compound.

$[\alpha]_D$ −58.82° (c 0.34, methanol) IR (KBr) 3295, 3066, 2958, 2873, 1717, 1642, 1539, 1194, 699 cm$^{-1}$ FDMS 430 (M$^+$), 430 (100) $^1$H NMR (300 MHz, CD$_3$OD) δ 0.82 (d, J=6.5 Hz, 3H), 0.87 (d, J=6.5 Hz, 3H), 1.40 (apparent t, J=7 Hz, 2H), 1.43–1.57 (m, 1H), 1.90 (s, 3H), 1.92–2.13 (m, 2H), 2.58–2.78 (m, 2H), 2.95 (dd, J=14, 9 Hz, 1H), 3.22 (dd, J=14, 5 Hz, 1H), 4.25 (apparent t, J=8 Hz, 1H), 4.55–4.67 (m, 2H), 7.12–7.27 (m, 5H) Analytical calculated for C$_{22}$H$_{30}$N$_4$O$_5$: C 61.38, H 7.2, N 13.01; found C 61.12, H 6.84, N 13.02

Example 6

[S-(R*,S*)]-5-(N-acetyl-L-leucinyl-L-phenylalanyl)amino-6-hydroxypiperidine-2-one and [S-(R*,R*)]-5-(N-acetyl-L-leucinyl-L-phenylalanyl)amino-6-hydroxypiperidine-2-one A 10 mL flask was charged with 91 mg (0.21 mmol) N-Acetyl-L-leucinyl-L-phenylalanyl-L-glutarimide and 2 mL 90% ethanol. The solution was cooled to 0° C. and 36 mg (0.96 mmol) NaBH$_4$ was added in one portion followed by 1 drop of concentrated HCl. The solution was stirred at 0° C., and an additional 1 drop of concentrated HCl was added after fifteen minutes. The reaction was then stirred at 0° C. for an additional two hours. The reaction mixture was then poured into 10 mL water and extracted three times with CHCl$_3$. The combined organic layers were dried over Na$_2$SO$_4$, filtered, and concentrated in vacuo. The residue was purified by rotary chromatography with 9:1 CH$_2$Cl$_2$/methanol to provide 53 mg (58%) of the title compound.

$[\alpha]_D$ −28.26° (C 0.46, methanol) IR (KBr) 3292, 3067, 2958, 2871, 2419, 1645, 1548, 1455, 1369, 1055, 700 cm$^{-1}$ FDMS 432 (M$^+$), 432 (100) 1H NMR (300 MHz, CD$_3$OD—mixture of diastereomers, diagnostic peaks only) δ 0.83–0.90 (m, 6H), 1.92 (s, 3H), 7.17–7.24 (m, 5H)

Preparation 14

N-Acetyl-L-valinyl-L-leucinyl-L-phenylalanyl-L-glutarimide

A solution of 58 mg (0.099 mmol) N-tert-Butoxycarbonyl-L-valinyl-L-leucinyl-L-phenylalaninyl-L-glutarimide in 1 mL CH$_2$Cl$_2$ and 150 μL TFA was prepared. The reaction was stirred for one hour and then concentrated in vacuo. The residue was then azeotroped twice with toluene and dissolved in 500 mL pyridine in a 10 mL round bottom flask under nitrogen. A syringe was used to introduce 9 μL acetic anhydride to the solution, and an additional 9 μL acetic anhydride was added after thirty minutes. After 2 hours of stirring, the reaction was concentrated in vacuo and partitioned between ethyl acetate and water. The water layer was acidified to pH=2 with 2N NaHSO4, and then the layers were separated. The organic layer was washed with brine, dried over $Na_2SO_4$, filtered, and concentrated in vacuo to afford 38 mg (72%) of a white powder.

$[\alpha]_D$ −50.00° (C 0.10, methanol) IR (KBr) 3290, 3070, 2961, 2933, 2873, 2421, 1714, 1639, 1541, 1369, 1198 cm$^{-1}$ FDMS 529(M$^+$), 529(100) 1H NMR (300 MHz CDCL$_3$), δ 0.81–0.89 (m, 12H), 1.42–1.57 (m, 3H), 1.90–2.09 (m, 6H), 2.64–2.72 (m, 2H), 2.96 (dd, J=14, 5 Hz, 1H), 3.19 (dd J=14, 5 Hz, 1H), 4.06 (d, J=7 Hz, 1H), 4.31–4.33 (m, 1H), 4.56–4.64 (m, 2H) 7.14–7.23 (m, 7H), 7.99 (d, J=8 Hz, 1H), 8.30 (d, J=8 Hz, 1H)

Example 7

[S-(R*,S*)]-5-(L-leucinyl-L-phenylalanyl)amino-6-hydroxypiperidine-2-one, and
[S-(R*,R*)]-5-(L-leucinyl-L-phenylalanyl)amino-6-hydroxypiperidine-2-one A 100 mL round bottom flask was charged with 1.83 g (3.74 mmol) N-tert-Butoxycarbonyl-L-leucinyl-L-phenylalaninyl-L-glutarimide, 30 mL dioxane, and 30 mL 5N HCl. The solution was stirred for thirty minutes and then concentrated in vacuo. The residue was placed on a vacuum pump for one hour, and then dissolved in 40 mL 90% ethanol. The solution was cooled to 0° C., and 780 mg (20.6 mmol) NaBH$_4$ was added in one portion followed by two drops of concentrated HCl. The solution was stirred at 0° C., and an additional 1 drop of concentrated HCl was added after fifteen minutes. The reaction was then stirred at 0° C. for an additional hour. The reaction mixture was then poured into 10 mL water and extracted three times with CHCl$_3$. The combined organic layers were dried over Na$_2$SO$_4$, filtered, and concentrated in vacuo. The residue was purified by rotary chromatography with 9:1 CH$_2$Cl$_2$/methanol to provide 620 mg (42%) of the title compound.

$[\alpha]_D$ +25.00° (c 0.68, methanol) IR (KBr) 3293, 3065, 2954, 2869, 1638, 1626, 1541, 700 cm$^{-1}$ FDMS 391(M$^+$), 391(100) $^1$H NMR (300 MHz, DMSO-d$_6$—major diastereomer given) δ 0.74 (d, J=6.5 Hz, 3H), 0.79 (d, J=6.5 HZ, 3H), 0.99–1.08 (m, 1H), 1.17–1.26 (m, 1H), 1.52–1.61 (m, 2H) , 1.95–2.09 (m, 4H), 2.24–2.34 (m, 1H), 2.75 (dd, J=13.5, 8.6 Hz, 1H), 2.89 (dd J=13.5 5.0 Hz, 1H) 3.06 (dd J=8.8, 5.0 Hz, 1H ), 3.74 (apparent d, J=2.9 Hz, 1H ), 4.48–4.50 (m, 1H), 4.56–4.60 (m, 1H), 5.90 (d, J=5.4 Hz, 1H), 7.12–7.22 (m, 5H), 7.87 (d, J=3.3 Hz, 1H), 8.00 (d, J=8.0 Hz, 1H), 8.11 (d, J=7.4 Hz, 1H)

Example 8

[S-(R*,S*)]-5-(L-valinyl-L-leucinyl-L-phenylalanyl)amino-6-hydroxypiperidine-2-one and
[S-(R*,R*)]-5-(L-valinyl-L-leucinyl-L-phenylalanyl)amino-6-hydroxypiperidine-2-one A 25 mL round bottom flask was charged with 500 mg (0.85 mmol) N-tert-Butoxycarbonyl-L-valinyl-L-leucinyl-L-phenylalaninyl-L-glutarimide, 5 mL CH$_2$Cl$_2$, and 750 µL TFA. The solution was stirred for three hours and then concentrated in vacuo. The residue was azeotroped twice with toluene, placed on a vacuum pump for one hour, and then dissolved in 8.5 mL 90% ethanol. The solution was cooled to 0° C., and 193 mg (5.1 mmol) NaBH$_4$ was added in one portion followed by one drop of concentrated HCl. The solution was stirred at 0° C., and an additional 1 drop of concentrated HCl was added after fifteen minutes. The reaction was then stirred at 0° C. for an additional hour. The reaction mixture was then poured into 10 mL water and extracted three times with CHCl$_3$. The combined organic layers were dried over Na$_2$SO$_4$, filtered, and concentrated in vacuo. The residue was purified by rotary chromatography with 3.2 CH$_2$Cl$_2$/methanol to provide 20 mg (5%) of the title compound.

FDMS 490 (M$^+$), 490 (100) $^1$H NMR (300 MHz, CD$_3$OD—major diastereomer given) δ 0.83–0.91 (m, 12H), 1.19–1.27 (m, 1H), 1.32–1.61 (m, 3H), 1.94 (dd, J=12.6, 6.3 Hz, 1H), 2.13–2.17 (m, 1H), 2.38 (dd, J=9.7, 6.3 Hz, 1H), 2.90 (dd, J=13.6, 9.1 Hz, 1H), 2.99 (dd, J=14.6, 7.7 Hz, 1H), 3.11–3.36 (m, 2H), 3.85–3.40 (m, 1H), 4.34 (dd, J=8.5, 6.1 Hz, 1H), 4.53–4.64 (m, 2H), 7.18–7.23 (m, 5H)

Example 9

In Vitro assay of HRV Protease Inhibition

HRV 3C protease was first activated by incubation with 0.03 mg/mL DTT for 30 minutes at 4° C. Twenty µL of activated protease (ranging from about 5 to about 12 U/mL wherein 1 U enzyme=the amount of protein required to hydrolyze 1 µmol of substrate per minute at 37° C.) in TBSA/DTT buffer (0.02M Tris, 0.15M NaCl, 0.01M DTT, 0.5 mg/mL bovine serum albumin (BSA); pH 8.0) were pipetted onto a 96-well polystyrene microtiter plate. Ten µL of potential inhibitory compound in 20% DMSO were added in varying concentrations to the enzyme and the mixture was incubated for one hour at 22° C. Then, 266 ng (20 µL) HRV 3C substrate, Biotin-arg-ala-glu-leu-gln-gly-pro-tyr-asp-glu-lys-(FITC)-OH (SEQ ID NO:1), in TBSA/DTT were added and the plate was incubated for eight hours at 22° C. The reaction mixture was diluted by the addition of 200 µL of TBSA/DTT. Twenty-five µL of a 0.1% solution of Fluoricon Avidin Assay Particles in TBSA 7.4 (0.02M Tris, 0.15M NaCl, 1 mg/mL BSA; pH 7.4) were added to each well of a 96-well Pandex Fluoricon Assay Plate and 20 µL of the diluted reaction mixture were added to each well. Unbound fluorescence was removed by filtration and subsequent washing with TBSA 7.4. Sample detection was performed by excitation at 485 nm and reading the resulting epifluorescence at 535 nm.

The results are shown in Table 1. IC$_{50}$ values reflect concentration (IC$_{50}$) of peptide inhibitor that gives a fluorescence intensity halfway between a substrate blank (reaction mixture containing no protease) and an enzyme control (protease plus substrate but no inhibitor).

Example 10

In Vitro Translation of HRV RNA

Complementary DNA derived from the HRV genome and representing the 2C'3ABCD portion of the HRV polyprotein precursor (Lee W, Monroe SS, Rueckert RR (1993) J. Virol. 67:2110–2122) was inserted into the commercially available pCITE vector (Novagen, 565 Science Dr., Madison, Wis.). The vector is supplied with the Novagen Red Nova® Lysate translation assay kit, which provides a lysate of New Zealand White rabbit reticulocytes along with other reagents, that allows for efficient cell-free synthesis of proteins from exogenous RNA templates.

The pCITE 2C'3ABCD-containing plasmid was used to transform the JM101 cell line (Stratagene, La Jolla, Calif.) which was then grown under standard conditions (5% CO$_2$, 37° C.) in 2x YT broth with ampicillin. The plasmid was then isolated by standard CsCl banding procedures.

The DNA was linearized by treating the plasmid with 2 units Mlu 1 restriction enzyme per µg DNA for 3 hours at 37° C., followed by proteinase K (50 µg/mL) treatment for 30 minutes at 37° C. The mixture was extracted twice with phenol/chloroform/isoamyl alcohol (1:1:1) followed by two extractions with chloroform/isoamyl alcohol (1:1). A 0.1 volume 3M sodium acetate (NaOAc), pH 5.2 and two volumes of 100% ethanol were added before placing at −80° C. for 60 minutes. The supernatant was decanted and the pellet was rinsed with 70% ethanol, dried under vacuum, and then resuspended in 25 µL Tris-EDTA buffer (10 mM Tris, 1 mM EDTA; pH 7.6).

The linearized DNA (1 µL) was diluted with water (18 µL) and heated at 56° C. for 2 minutes. A mixture of the four ribonucleotides (2.5 mM; 8 µL) was added along with transcription buffer (200 mM Tris-HCl, 50 mM NaCl, 30 mM MgCl, 10 mM spermidine; pH 7.9) (8 µL), 100 mM DTT (4 µL), and T7 polymerase (1 µL; 50 U/mL). The ingredients were mixed, incubated at 37° C. for 60 minutes, treated with RNase-free DNase, and incubated at 37° C. for 10 more minutes. The resulting RNA was extracted twice with phenol/chloroform/isoamyl alcohol (1:1:1) followed by an extraction with chloroform/isoamyl alcohol (1:1). 20 µL of 7.5M ammonium acetate ($NH_4OAc$) and 150 µL ethanol were added and the mixture was centrifuged after standing for 5 minutes. The pellet was washed with 70% ethanol, dryed under vacuum, and resuspended in water (40 µL).

The compounds of Formula I were assayed according to the Red Nova protocol for their ability to inhibit translation of the rhinoviral RNA by the reticulocyte lysate. $^3$H-Leucine (5 mCi/mL) was included in the assay mixture so that translation products could be identified by autoradiography when the samples were analyzed by SDS polyacrylamide gel electrophoresis.

Autoradiography demonstrated that when no inhibitors were present, the translated viral polyprotein was processed by its auto-proteolytic activity into the several individual proteins. When the Formula I inhibitors of Examples 5 and 6 were included in the assay, the translated polyprotein appeared as a single unprocessed band indicating that the proteolytic activity of the polyprotein-was inhibited. The Formula I inhibitor of Example 7 was toxic at the dose tested.

containing Earl's balanced salt solution, 1% fetal bovine serum, penicillin (150 units/mL) and streptomycin (150 µg/mL). The cells were incubated overnight at 37° C. in 5% $CO_2$ atmosphere, and then infected with HRV. After allowing the virus to adsorb to the cells for 1–2 hours, medium containing serial dilutions of inhibitor or medium alone was added to the wells. After further incubation for 2–3 days the antiviral effect (the ability to prevent viral cytopathic effect) of the inhibitors was assessed by measurement of mitochondrial enzyme activity according to Scudio, et al. (1988) Cancer Res. 48:4827–33.

Assessment was done by adding 50 µL of XTT/PMS in PBS (1 mg/mL 2,3-bis(methoxy-4-nitro-5-sulfophenyl)-2H-tetrazolium-5-carboxanilide, inner salt, sodium salt (XTT—Sigma, St Louis); 25 µM phenazine methosulfate (PMS); phosphate buffered saline (PBS)) to each of the microtiter wells. The cultures were incubated at 37° C. in 5% $CO_2$ atmosphere until a color change was prominent, and absorbance was measured at 450 nM. The concentration of inhibitor required to inhibit the development of a viral-induced cytopathic effect by 50% ($IC_{50}$) (µg/mL) was then determined from the linear portion of each dose response curve. These results are reported in Table 1 below.

TABLE 1

| Example # | $IC_{50}$ | Translation Assay | Whole Cell Antiviral Testing |
|---|---|---|---|
| 1 | >40 | NT | NT |
| 2 | >40 | NT | NT |
| 3 | 15 | NT | NT |
| 4 | >10 | NT | NT |
| 5 | 0.2–0.8 | ++++ (5–10 µg/mL) | ++ (500 µg/mL) |
| 6 | 1.4 | ++ (100 µg/mL) | NT |
| 7 | 0.3–1 | toxic | toxic |
| 8 | 2 | NT | NT |

NT = Not Tested
− = negative results
+ = positive to strongly positive
(concentrations tested in translation assay and whole cell assay are indicated in parentheses)

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) TOPOLOGY: linear ( i i ) MOLECULE TYPE: protein ( x i ) SEQUENCE DESCRIPTION: SEQ ID NO:1:

arg — ala — glu — leu — gln — gly — pro — tyr — asp — glu — lys
1                    5                     10

Example 11

Whole Cell Culture Assay of Anti-HRV Activity

Hela cells were dispersed in a 96-well tissue culture plate at 20,000 cells per well with minimum essential medium

We claim:

1. A process for preparing a compound of Formula I

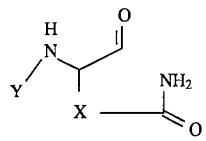

wherein

X is $(CR^1CR^2)n$;

Y is an amino acid sequence of 3 or less amino acid residues, an amino-protecting group, or $-C(O)R^3$;

n is 2;

$R^1$ is hydrogen and $R^2$ is hydrogen or alkyl;

$R^3$ is hydrogen, alkyl, arylalkyl, heteroarylalkyl, aryl, alkylaryl, heteroaryl, alkylheteroaryl, alkoxy, cycloalkoxy, arylalkoxy, heteroarylalkoxy, aryloxy, heteroaryloxy, cycloalkyl, heterocyclic, heterocycloxy, alkylamino, cycloalkyamino, arylamino, heterocycloamino, cycloalkylmethoxy, arylmethoxy, heterocyclomethoxy, alkylmethylamino, arylmethylamino or hetercyclomethylamino, which comprises regioselectively reducing an imide of Formula III in the presence of $NaBH_4$ and an acidified hydroxylic solvent

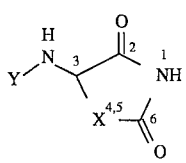

such that reduction at the 2-position of said imide occurs to a greater extent than reduction at the 6-position, and wherein X and Y have the meanings given for Formula I.

2. A process as claimed in claim 1 having the additional steps of:

a) deprotecting the intermediate of Formula III to generate an intermediate of Formula IV

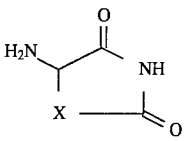

b) acylating an intermediate of Formula IV with a compound of Formula V

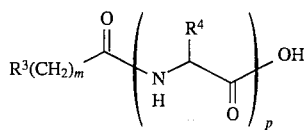

to generate an intermediate of Formula VI

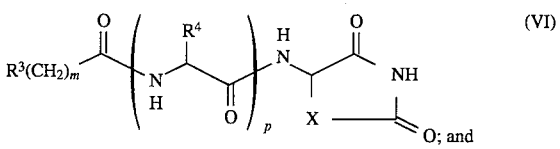

c) reducing the intermediate of Formula VI to generate a compound of Formula Ia

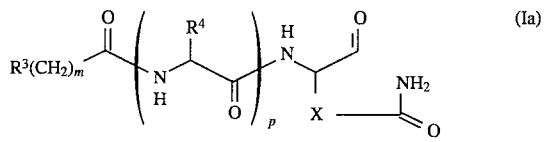

wherein in each of Formulas V, VI and Ia $R^4$ is an amino acid side chain;

m is 0, 1, 2, 3, or 4;

p is 0, 1, 2, 3, 4, or 5; and when p is greater than 1, the identity of each $R^4$ is independent of the other $R^4$ side chains.

3. A process as claimed in claim 2 having the additional step of deprotecting the intermediate of Formula VI before reducing to generate a compound of Formula Ib

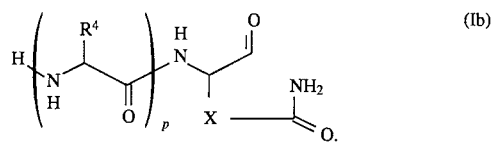

4. A process as claimed in claim 1 having the additional step of acid activating a compound of Formula II

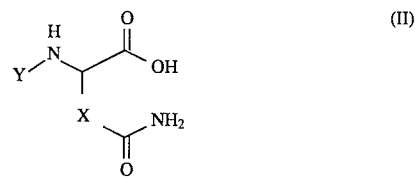

5. A process as claimed in claim 1 wherein the relative molar amount of $NaBH_4$ to imide is 1:1 to 5:1.

6. A process as claimed in claim 1 wherein the temperature is between about 0° C. and about 10° C.

7. A process as claimed in claim 1 wherein the temperature is about 0° C.

8. A process as claimed in claim 1 wherein the hydroxylic solvent has an aqueous content.

9. A process as claimed in claim 8 wherein the hydroxylic solvent is 90% ethanol.

* * * * *